(12) United States Patent
Ge et al.

(10) Patent No.: US 12,576,031 B2
(45) Date of Patent: Mar. 17, 2026

(54) MAGNETIC WIRE FOR RETRIEVAL AND ELIMINATION OF CALCULUS FROM THE URINARY TRACT

(71) Applicants: The Board of Trustees of the Leland Stanford Junior University, Stanford, CA (US); U.S. Government as represented by the Department of Veterans Affairs, Washington, DC (US)

(72) Inventors: Tianjia Jessie Ge, Sunnyvale, CA (US); Simon Conti, Stanford, CA (US); Joseph C. Liao, Redwood City, CA (US); Kunj Raju Sheth, San Francisco, CA (US); Shan X. Wang, Portola Valley, CA (US)

(73) Assignees: The Board of Trustees of the Leland Stanford Junior University, Stanford, CA (US); U.S. Government as represented by the Department of Veterans Affairs, Washington, DC (US)

( * ) Notice: Subject to any disclaimer, the term of this patent is extended or adjusted under 35 U.S.C. 154(b) by 105 days.

(21) Appl. No.: 18/397,947

(22) Filed: Dec. 27, 2023

(65) Prior Publication Data

US 2024/0207188 A1 Jun. 27, 2024

Related U.S. Application Data

(63) Continuation of application No. 17/524,603, filed on Nov. 11, 2021, now Pat. No. 11,903,666.
(Continued)

(51) Int. Cl.
*A61K 9/14* (2006.01)
*A61B 17/00* (2006.01)
(Continued)

(52) U.S. Cl.
CPC .............. *A61K 9/14* (2013.01); *A61B 17/221* (2013.01); *A61B 34/73* (2016.02); *A61K 9/0034* (2013.01);
(Continued)

(58) Field of Classification Search
CPC .......... A61B 17/221; A61B 2017/2212; A61B 2017/2215; A61B 2017/2217;
(Continued)

(56) References Cited

U.S. PATENT DOCUMENTS

| | | |
|---|---|---|
| 1,006,453 A | 10/1911 | Ashworth |
| 9,925,311 B2 | 3/2018 | Grunwald et al. |

(Continued)

FOREIGN PATENT DOCUMENTS

| | | |
|---|---|---|
| EP | 3348287 A1 | 7/2018 |
| EP | 4522062 A2 | 3/2025 |

(Continued)

OTHER PUBLICATIONS

International Search Report and Written Opinion for International Application No. PCT/US2023/067006, Search completed Dec. 5, 2023, Mailed Feb. 2, 2024, 29 Pgs.
(Continued)

*Primary Examiner* — Kankindi Rwego
(74) *Attorney, Agent, or Firm* — KPPB LLP

(57) ABSTRACT

A medical device for retrieval of kidney stone fragments from a urinary tract is provided. The medical device has a plurality of magnets arranged within a flexible sheath forming a flexible wire. The magnets are magnetically attached end-to-end and arranged with their magnetic polarities alternating in direction. The magnetization direction of each of the magnets is orthogonal to the length axis of the flexible wire. A removable inner stylet is situated within the flexible sheath allowing for modifiable flexibility of the wire. The
(Continued)

LENGTH OF WIRE medical device is dimensioned to be introduced into the urinary tract and standard endoscopic devices. The medical device is further dimensioned to allow for the wire with magnetically attached stone fragments to be retrieved from the urinary tract. The magnetic field along the length axis is sufficient to attract to the surface of the flexible wire superparamagnetic nanoparticles which have bound themselves to kidney stone fragments.

23 Claims, 7 Drawing Sheets

Related U.S. Application Data

(60) Provisional application No. 63/116,324, filed on Nov. 20, 2020.

(51) Int. Cl.
| | |
|---|---|
| *A61B 17/22* | (2006.01) |
| *A61B 17/221* | (2006.01) |
| *A61B 34/00* | (2016.01) |
| *A61K 9/00* | (2006.01) |

(52) U.S. Cl.
CPC .................. *A61B 2017/0034* (2013.01); *A61B 2017/00876* (2013.01); *A61B 2017/22082* (2013.01); *A61B 2034/731* (2016.02)

(58) Field of Classification Search
CPC .. A61B 2017/0034; A61B 2017/00876; A61B 2017/22082; A61B 34/73; A61B 2034/731; A61K 9/0034; A61K 9/14
USPC .................................................. 606/127, 128
See application file for complete search history.

(56) References Cited

U.S. PATENT DOCUMENTS

| | | | |
|---|---|---|---|
| 9,974,554 | B2 | 5/2018 | Antonelli et al. |
| 10,064,653 | B2 | 9/2018 | Vermesh et al. |
| 10,232,079 | B2 | 3/2019 | Grunwald et al. |
| 10,828,414 | B2 | 11/2020 | Mabray et al. |
| 11,903,666 | B2 | 2/2024 | Ge et al. |
| 2002/0119116 | A1 | 8/2002 | Sahatjian et al. |
| 2009/0136594 | A1 | 5/2009 | McLeroy et al. |
| 2016/0074561 | A1* | 3/2016 | Grunwald ............... A61P 13/04 |
| | | | 606/127 |
| 2016/0270805 | A1 | 9/2016 | Walish et al. |
| 2016/0354116 | A1 | 12/2016 | Vermesh et al. |
| 2017/0119411 | A1 | 5/2017 | Shah |
| 2018/0280039 | A1 | 10/2018 | Sun |
| 2019/0282247 | A1 | 9/2019 | Shelton |
| 2022/0125570 | A1 | 4/2022 | Stifelman et al. |
| 2022/0160450 | A1 | 5/2022 | Ge et al. |

FOREIGN PATENT DOCUMENTS

| | | | |
|---|---|---|---|
| WO | 2023220755 | A2 | 11/2023 |
| WO | 2023220755 | A3 | 3/2024 |

OTHER PUBLICATIONS

Chen et al., "DOX@Ferumoxytol-Medical Chitosan as Magnetic Hydrogel Therapeutic System for Effective Magnetic Hyperthermia and Chemotherapy in Vitro", Colloids Surf B Biointerfaces, Jun. 2020;190:110896. doi: 10.1016/j.colsurfb.2020.110896.

Ge et al., "A magnetic hydrogel for the efficient retrieval of kidney stone fragments during ureteroscopy", Nature Communications, vol. 14, 3711, Published online Jun. 22, 2023, DOI: 10.1038/s41467-023-38936-1.

Tan et al., "In vitro comparison of prototype magnetic tool with conventional nitinol basket for ureteroscopic retrieval of stone fragments rendered paramagnetic with iron oxide microparticles", J Urol. Aug. 2012;188 (2):648-52. doi: 10.1016/j.juro.2012.03.118.

Vermesh et al., "An intravascular magnetic wire for the high-throughput retrieval of circulating tumour cells in vivo", Nat Biomed Eng. Sep. 2018, 2(9): 696-705. doi:10.1038/s41551-018-0257-3.

International Preliminary Report on Patentability for International Application PCT/US2023/067006, Report issued Nov. 7, 2024, Mailed Nov. 28, 2024, 7 Pgs.

\* cited by examiner a)

b)

LENGTH OF WIRE

LENGTH OF WIRE a)

500

510

520

MAGNETIC WIRE FOR RETRIEVAL AND ELIMINATION OF CALCULUS FROM THE URINARY TRACT

CROSS-REFERENCE TO RELATED APPLICATIONS

This application is a continuation of U.S. patent application Ser. No. 17/524,603 filed Nov. 11, 2021 and issued as U.S. Pat. No. 11,903,666 on Feb. 20, 2024, which claims priority from U.S. Provisional Patent Application 63/116,324 filed Nov. 20, 2020. The disclosures of which are hereby incorporated by reference in their entirety.

STATEMENT OF FEDERALLY SPONSORED RESEARCH

This invention was made with Government support under contract DK131776 awarded by the National Institutes of Health. The Government has certain rights in the invention.

FIELD OF THE INVENTION

The invention relates to medical devices and methods for retrieval and elimination of calculus (stone fragments) from the urinary tract.

BACKGROUND OF THE INVENTION

Nephrolithiasis, or kidney stone disease, affects 8-9% of the population and accounts for >$2 billion of healthcare expenditures per year in the USA alone. Stones can be located anywhere within the urinary tract (kidney, ureter, bladder, or urethra). Untreated stone disease has the potential to cause pain, infection, and loss of kidney function. Surgical management of stone disease frequently involves ureteroscopy and laser lithotripsy, in which a ureteroscope is passed endoscopically through the urethra, bladder, and ureter, up to the stone, and a laser fiber is passed through the working channel of the ureteroscope to fragment and/or 'dust' the stone. Fragmentation and 'active retrieval' involve using the laser fiber to fragment a stone into several smaller pieces (generally 2-4 mm in size) which are individually retrieved with a wire basket and removed from the body. 'Dusting' utilizes a different technique and laser setting to generate tiny dust-like fragments which can theoretically be passed spontaneously by the patient's body.

Rendering a patient 'stone-free' is the best way to prevent further complications or re-interventions (stone-related events) due to residual stone fragments that can re-obstruct the ureter or grow in size. Active retrieval of stone fragments is associated with a higher stone-free rate (SFR) compared to dusting (58.2% vs 74.3%), but has significantly longer operative time (67 min vs 37 min, costing on average $1343 more) due to the time spent retrieving each fragment individually. Dusting is faster, a large stone may generate such a large amount of 'dust' that it obscures the view of the remaining stone, causing the surgery to be stopped prematurely due to lack of visualization and necessitating a second surgery. In addition, the presumption that small dust-like fragments will pass spontaneously is not always accurate, especially in patients with limited mobility.

Residual stone fragments less than 2 mm in size are commonly deemed 'clinically insignificant' or unlikely to cause stone-related events, thus the clinical definition of 'stone-free' is commonly accepted to mean no residual stone fragments larger than 2 mm in size. However, while larger fragments are more likely to cause stone-related events, there is still a 20-30% rate of stone-related events associated with fragments <2 mm in size.

There have been many different configurations of wire baskets developed to increase the efficiency of stone retrieval, but these are all limited by being ill-suited to capture and retrieve multiple stone fragments at once, inability to capture small fragments, and reliance on the surgeon to guide the basket very precisely to the stone. Tan et al. (J Urol. 2012 188(2):648-52) attempted to magnetize kidney stone fragments with paramagnetic nanoparticles, for retrieval with a magnetic tool. Their prototype magnetic tool was a single magnet measuring 8 Fr (2.54 mm) in diameter, with efficacy limited by poor visualization due to the large size of the magnet, and decoupling of fragments from the magnet due to low magnetic forces.

U.S. Pat. No. 1,006,453 by Stanford University demonstrated a magnetic wire for intravascular retrieval and enrichment (MagWIRE) which has alternating polarity magnets within a flexible sheath. The MagWIRE generates magnetic forces orders of magnitude greater than a conventional single polarity magnet. This was used in conjunction with superparamagnetic nanoparticles which could bind with disease-associated biomarkers in the bloodstream, to perform intravascular retrieval and enrichment of biomarkers from the bloodstream. The magnetic tool was slim (0.75 mm) and flexible, allowing it to be used within a small blood vessel.

SUMMARY OF THE INVENTION

The present invention provides a medical device for retrieval of kidney stone fragments from a urinary tract. Kidney stone fragments include calcium, uric acid, struvite, cystine or a combination thereof. The medical device has a plurality of magnets arranged within a flexible sheath forming a flexible wire. The magnets are magnetically attached end-to-end and arranged with their magnetic polarities alternating in direction. The magnetization direction of each of the magnets is orthogonal to the length axis of the flexible wire. A removable inner stylet is situated within the flexible sheath allowing for modifiable flexibility of the wire. The medical device is dimensioned to be introduced into the urinary tract and standard endoscopic devices. The medical device is further dimensioned to allow for the wire with magnetically attached stone fragments to be retrieved from the urinary tract. The magnetic field along the length axis is sufficient to attract to the surface of the flexible wire superparamagnetic nanoparticles which have bound themselves to kidney stone fragments.

In one example, the magnets are cylindrical or ring-shaped magnets each having a diametric magnetization.

In another example, the magnets are cylindrical or ring-shaped magnets having an outer diameter of 0.2 mm to 10 mm.

In yet another example, the alternating end-to-end polarities alternate 180 degrees or alternate with a rotation from magnet to magnet at 45-180 degrees increments.

In yet another example, the medical device has non-magnetic spacers between each of the magnets.

In yet another example, each of the plurality of magnets has a length in a range of 0.5 mm to 10 cm.

In yet another example, the medical device contains 10 to 1000 magnets.

In yet another example, the flexible wire generates magnetic field gradients of 100 to 10,000 T/m.

In yet another example, multiple flexible magnetic wires are combined to create a magnetic wire basket.

In yet another example of the medical device, the sheath of the flexible wire incorporates bristles or structures to shield and promote retention of a magnetically attached stone fragment.

The present invention further provides a method for retrieval of kidney stone fragments from a urinary tract. Superparamagnetic particles are inserted into the urinary tract. The superparamagnetic particles bind themselves to calculi. A flexible magnet wire is inserted into a urinary tract. The flexible wire has a plurality of magnets arranged within a flexible sheath forming the flexible magnet wire. The magnets are magnetically attached end-to-end and arranged with their magnetic polarities alternating in direction. The magnetization direction of each of the magnets is orthogonal to the length axis of the flexible magnet wire. The magnetic field along the length axis is sufficient to attract to the surface of the flexible magnet wire superparamagnetic particles which have bound themselves to the calculi. The superparamagnetic particles bound to the calculi are removed from the urinary tract.

In one example, the superparamagnetic particles are delivered with a hydrogel polymer. In a further example, the hydrogel polymer is capable of binding to the calculi such that crosslinking the hydrogel polymer results in a magnetic hydrogel that coats and binds the calculi.

The present invention still further provides a device or method for retrieval of stone fragments from a urinary tract. Here the device or method are an improvement on an existing device or method, as described in U.S. Pat. No. 1,006,453, but now herein for retrieval of stone fragments from a urinary tract wherein the improvement comprises using the MagWIRE as described herein for the purposes retrieval of stone fragments from a urinary tract and with the additional structural elements and method steps.

Embodiments of the invention have several advantages. First, the MagWIRE can retrieve multiple fragments from the body on a single pass, compared to the conventional wire baskets which generally are limited to one fragment per pass. The unique geometry of alternating-polarity magnetic units maintains strong magnetic field gradients (100-10,000 T/m) along the entire wire. Thus, multiple stone fragments can be collected along the entire length of the magnetic tip of the device, rather than just at the very end of the magnet as is the case with conventional single polarity magnets, greatly increasing the yield. Additionally, the strong magnetic field of the MagWIRE means that stone fragments must only be in the general vicinity to be captured, improving the ease of operability. The predominant basket retrieval technique requires great precision on the surgeon's part to open and close the basket around a stone, which can be time-consuming and generally requires a second assistant to operate the basket. The magnetic wire could be operated by a single person, just by deflecting the tip of the ureteroscope to guide it around the kidney/ureter/bladder to attract stones. Alternatively, in an embodiment where the magnetic wire is part of a basket configuration, the magnetic forces can simplify the process of capturing a magnetically-labeled stone in the basket. The MagWIRE can greatly increase the speed of fragment retrieval and shorten operative times, decreasing costs and exposure to general anesthesia. Secondly, the MagWIRE can capture stone fragments that are too small to be grasped by a conventional wire basket. These fragments are typically left in the body due to the inability to actively remove them and assumed to pass spontaneously in the patient's urine. However, this assumption is not always true and can result in complications and re-interventions for residual fragments. The MagWIRE can improve the stone-free rates for kidney stone surgeries and improve patient outcomes. Third, the flexibility and dimension of this MagWIRE greatly resembles the guidewires which are already commonly used for ureteroscopy. The flexible tip allows it to be inserted into the urinary tract without causing trauma. The dimension makes it easily compatible with existing equipment. In addition, the removal inner stylet provides even greater control over the flexibility, and can optimize the flexibility of the ureteroscope tip while the medical device is in place. Fourth, while the strong magnetic field will attract a magnetically-labeled fragment to the device, if significant resistance is met upon withdrawal of the device with an attached fragment, the resisting force will remove the fragment from the magnet rather than cause damage to the urinary system. This is of utmost importance in the ureter. For example, a basket containing a stone which is too large to pass through the ureter could cause the dreaded complication of ureteral avulsion if it is withdrawn with significant resistance. In addition, it can be quite difficult to disengage a basket from the stone it is surrounding, if there is no room in the ureter to fully open the basket. The magnetic medical device will avoid this complication by only retaining the number of fragments which are small enough to be safely removed from the ureter, and easily shedding the rest. In one embodiment as described above, the magnets can be removed from the sheath to completely remove the magnetic force and disengage the device from the stone fragments.

BRIEF DESCRIPTION OF THE DRAWINGS

FIG. 2A shows a colorimetric scale of the magnetic field gradient ∇B (T/m) which decays radially from the wire surface. The axial configuration has high gradients only at the ends of the wire, while the alternating configuration has high gradients to attract magnetic particles across the entire length, and the Halbach configuration has high gradients across the entire length but only on one side of the magnet. FIG. 2B plots the decay of the magnetic field gradient as distance increases from the magnet surface. The alternating polarity and Halbach configurations outperform the axial configuration by orders of magnitude.

DETAILED DESCRIPTION

Figure 1:
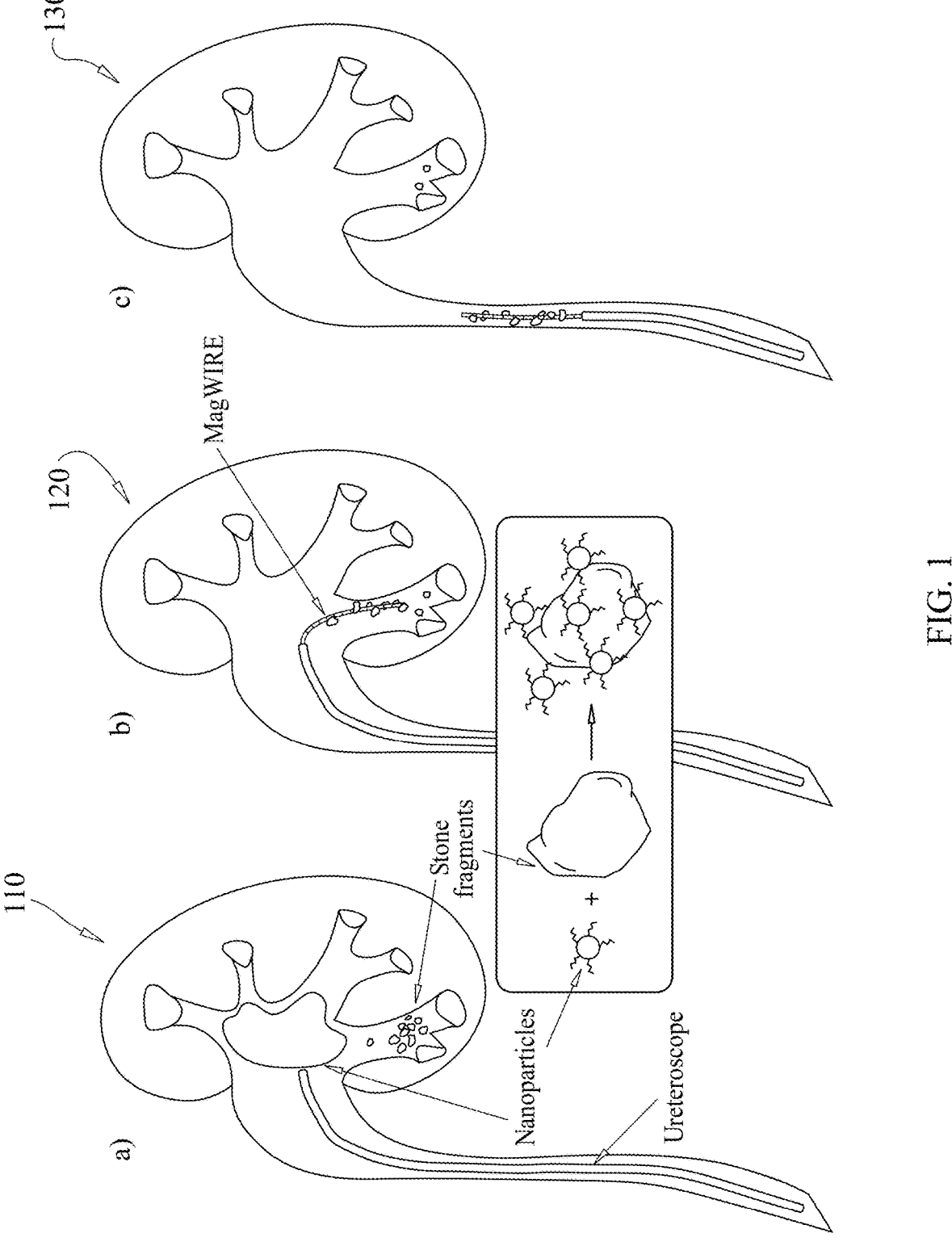
FIG. 1 shows an overview according to an exemplary embodiment of the invention the MagWIRE device and method for retrieval of stone fragments from the urinary system. 110 shows stone fragments within the collecting system of a kidney. A ureteroscope is inserted up the ureter to the kidney, and functionalized nanoparticles are instilled into the collecting system, which then bind to the stone fragments. 120 shows the flexible MagWIRE introduced through the working channel of the ureteroscope, magnetically attracting the superparamagnetically-labeled stone fragments. 130 shows the MagWIRE and ureteroscope being withdrawn from the ureter, along with the magnetically bound stone fragments.
Figure 2A:
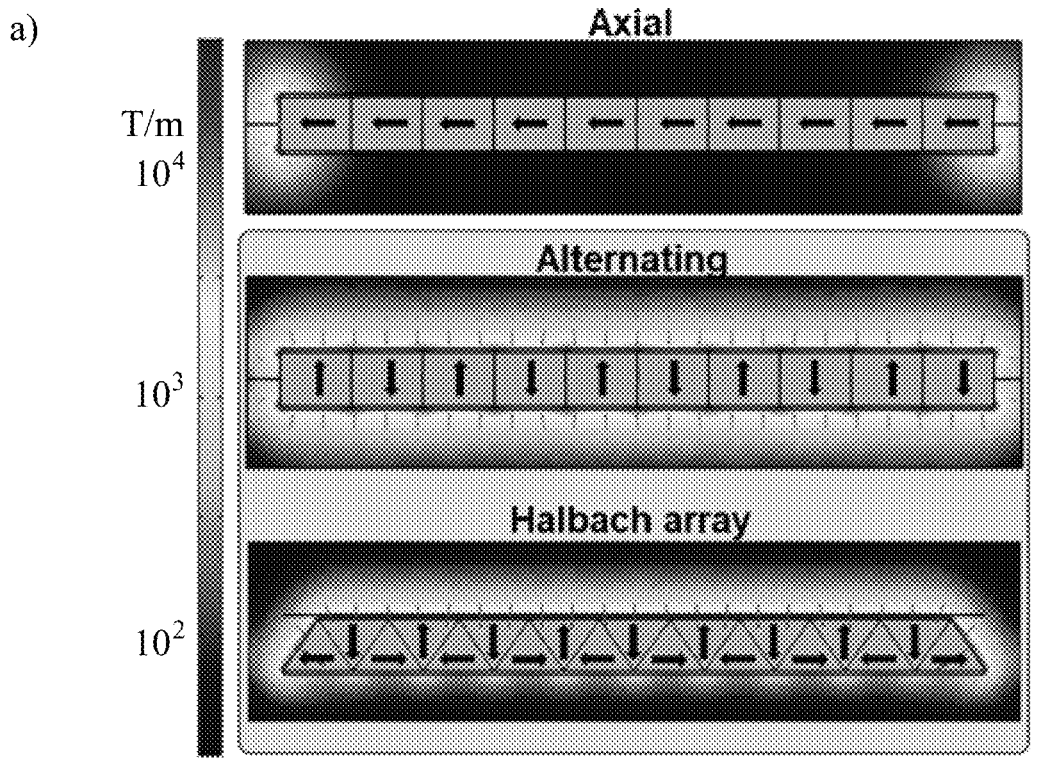
FIGS. 2A-B show according to an exemplary embodiment of the invention a simulation of magnetic field gradients for different magnetic configurations (black arrows shown within the magnets point north).
Figure 2B:
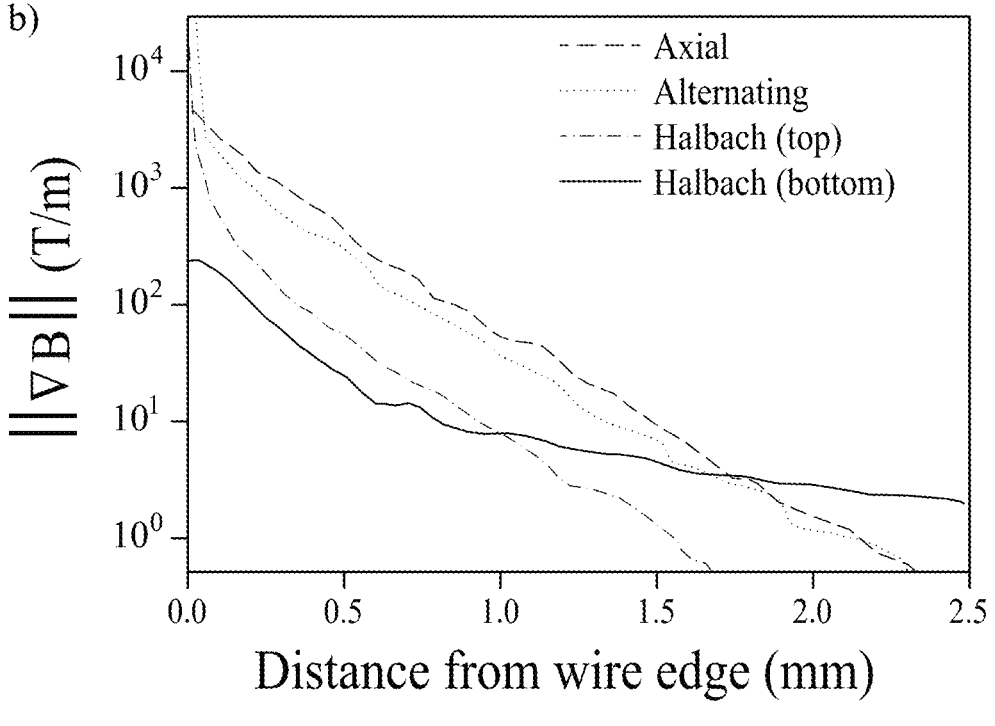
Figure 3:
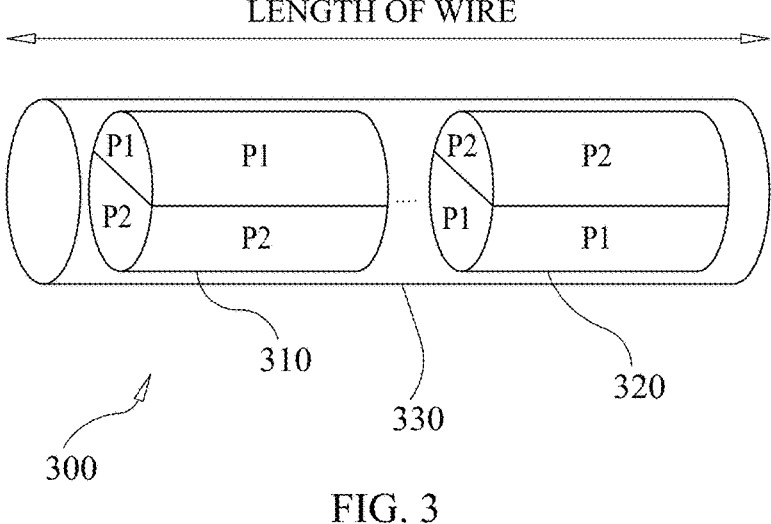
FIG. 3 shows according to an exemplary embodiment of the invention an exploded view of the MagWIRE according to an exemplary embodiment of the invention. A plurality of magnets (here shown two, 310, 320) are arranged within flexible sheath 330 forming a flexible wire 300. The magnets are magnetically attached end-to-end (i.e. they are not separated from each other) and arranged with their magnetic polarities alternating in direction (P1 and P2 are alternating polarities). The magnetization direction of each of the magnets is orthogonal to the length axis of the flexible wire.
Figure 4:
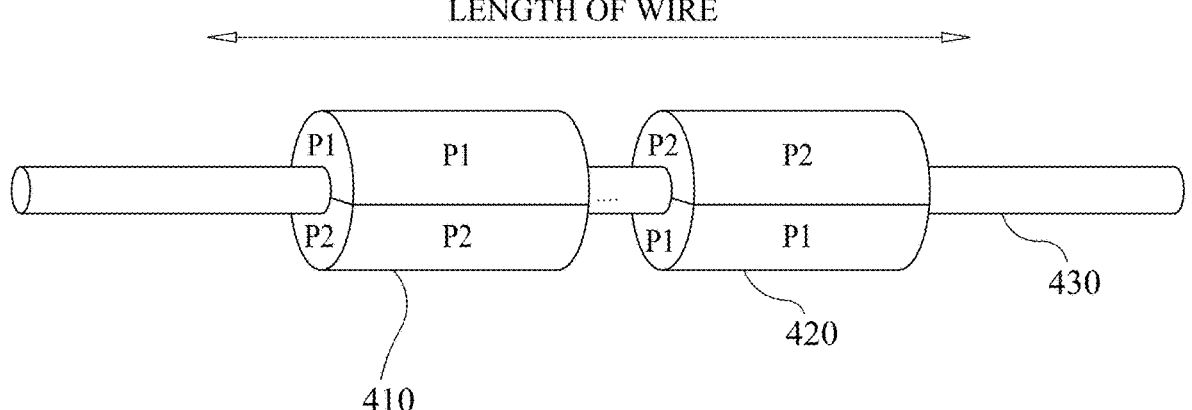
FIG. 4 shows according to an exemplary embodiment of the invention an exploded view of the MagWIRE according to an embodiment of the invention where the magnets are ring-shaped. A plurality of magnets (here shown two, 410, 420) are arranged with a central wire 430 to provide structural stability. There is no outer sheath. The magnets are similarly arranged end-to-end with their magnetic polarities alternating in direction (P1 and P2 are alternating polarities). The magnetization direction of each of the magnets is orthogonal to the length axis of the flexible wire.
Figure 5:
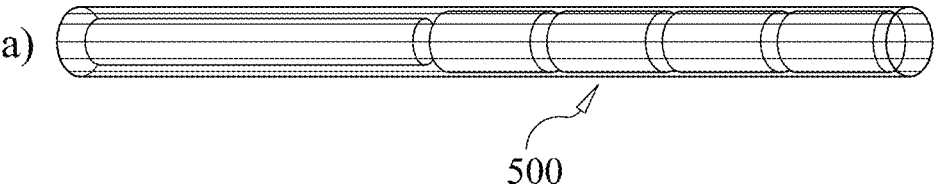
FIGS. 5A-C show according to an exemplary embodiment of the invention a view of the MagWIRE with its removable inner stylet. A plurality of magnets (here shown four) are arranged within flexible sheath 520 forming a flexible wire 500, with a stiff inner stylet 510 (FIG. 5A). The magnetic tip can easily bend because the magnets are held together only by magnetic forces (FIG. 5B). If the inner stylet is removed, the MagWIRE becomes more flexible (FIG. 5C).
Figure 5:
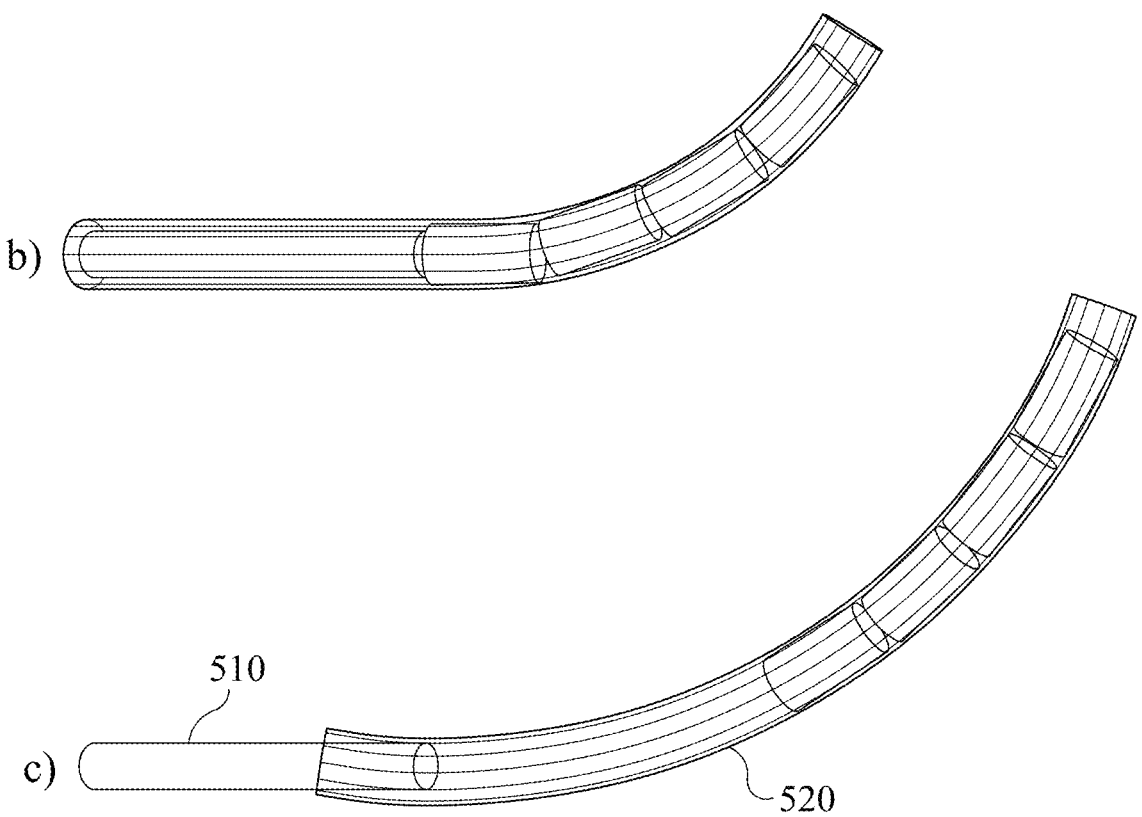
Figure 6:
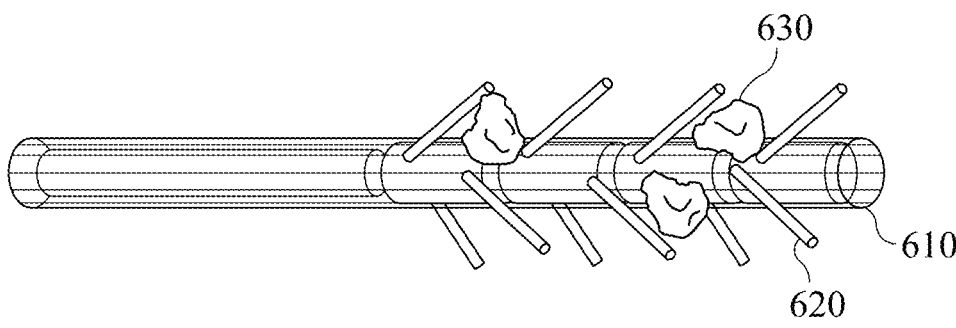
FIG. 6 shows according to an exemplary embodiment of the invention a view of the MagWIRE where the flexible sheath 610 additionally has flexible bristles 620 on its surface to shield magnetically attracted stone fragments 630 from forces that could knock the fragment loose from the wire. Examples include the wire contacting and scraping against the side of the ureter or ureteral access sheath, or the force required to break the surface tension of water when passing through an air bubble.
Figure 7:
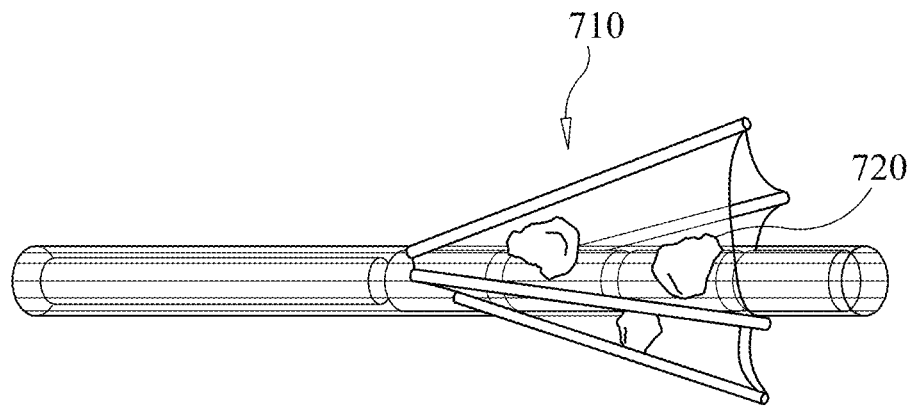
FIG. 7 shows according to an exemplary embodiment of the invention a view of the MagWIRE where the flexible sheath additionally has a retractable shield 710 on its surface to shield magnetically attracted stone fragments 720 from forces that could knock the fragment loose from the wire, as described in FIG. 6.
Figure 8:
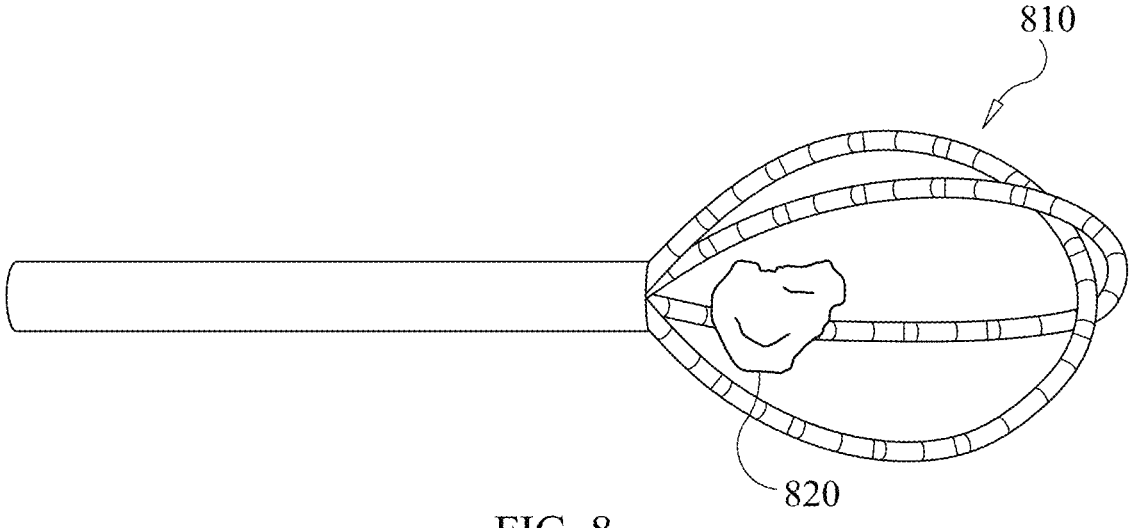
FIG. 8 shows according to an exemplary embodiment of the invention a view where the MagWIRE is fashioned into a wire basket 810 to improve the ease of capturing a magnetically labeled stone fragment 820.
Figure 9:
FIG. 9 shows according to an exemplary embodiment of the invention a scanning electron microscopy image of superparamagnetic particles (3.5 μm in diameter) attached to the surface of a calcium oxalate kidney stone fragment.
Figure 10:
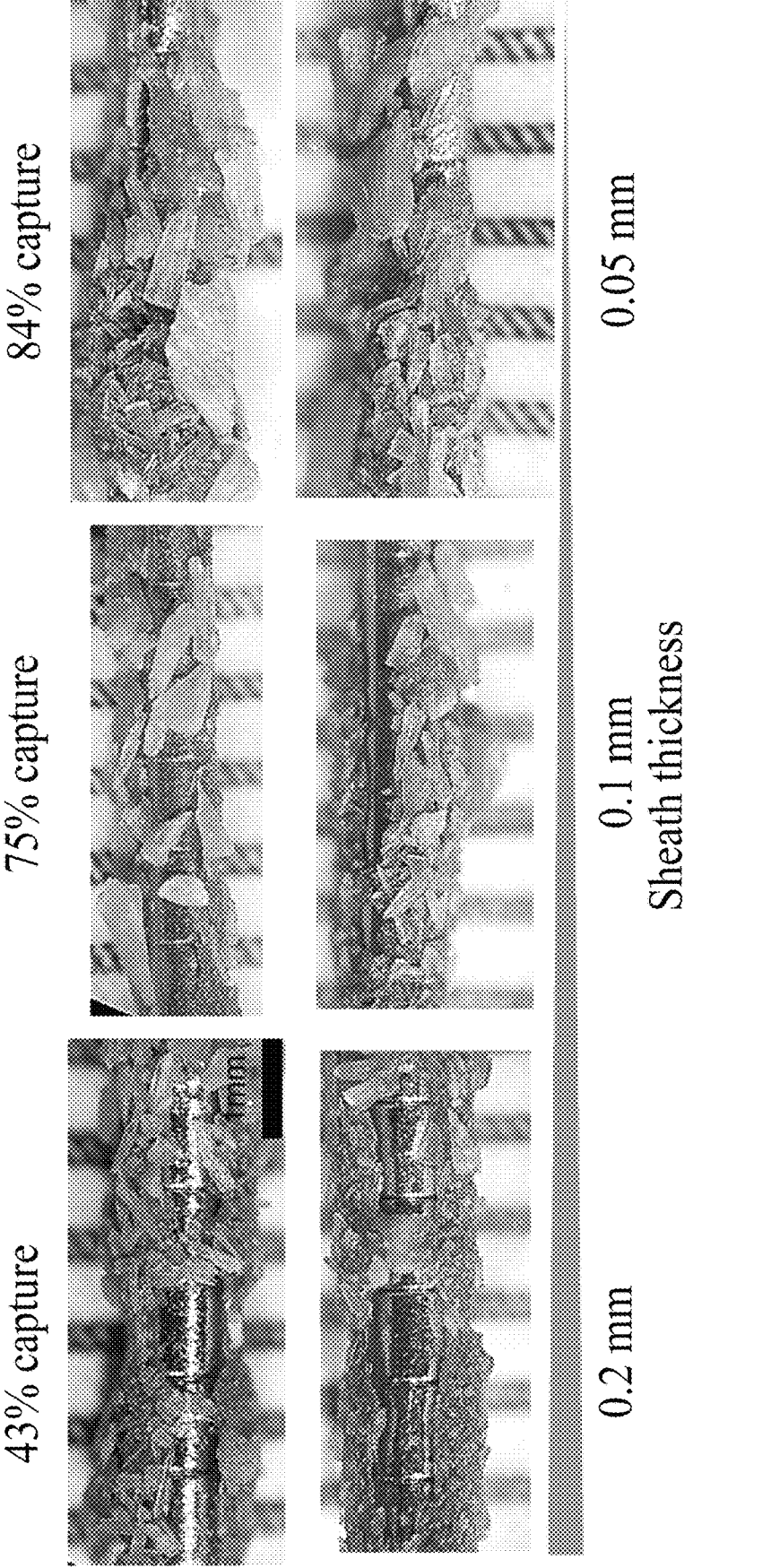
FIG. 10 shows according to an exemplary embodiment of the invention MagWIREs with sheaths of different thicknesses used to capture magnetically labeled stone fragments <1 mm in size. As represented in FIG. 2$b$, a wire with a 0.2 mm sheath will have a lower magnetic gradient at the sheath surface compared to a wire with a 0.05 mm sheath. Accordingly, wires with thinner sheaths capture a greater number of fragments, and capture larger fragments.

In this invention, a device and method are provided to allow the MagWIRE technology to be used within the urinary tract for more efficient and complete retrieval of super-paramagnetically-labeled stone fragments, with the following modifications: 1) The device shall have a removable inner stylet to allow for both a stiff wire body with a flexible tip that can be easily loaded into the working channel of a ureteroscope, as well as a flexible wire body that will not interfere with the flexion of the ureteroscope tip when navigating the urinary system. The requirement for a both stiff and flexible wire body was not present in the previous intravascular iteration. 2) Macroscopic stone fragments are more likely to fall off or be knocked off of the wire compared to microscopic biomarkers in the previous iteration, as they are subject to increased gravitational, shear, drag, and surface tension forces. Therefore, the device may include modifications such as soft 'bristles' on the surface of the wire to aid in stone fragment retention and retrieval, or other deployable shields to prevent magnetically-attached stone fragments from falling off. 3) Macroscopic stone fragments also have a lower surface area-to-volume ratio and greater density compared to microscopic biomarkers. Thus, the attractive magnetic force of a stone fragment with a surface coating of superparamagnetic particles will eventually be outweighed by the countering gravitational force, which is a consideration not applicable to microscopic biomarkers. Thus, the method may require modifications to increase the number of particles labeling a fragment. The superparamagnetic particles may be delivered in a hydrogel format in order to increase the density of particles and effective magnetic moment of the labeled stone fragment, improving magnetic capture rates and allowing capture of larger fragments. 4) One or magnetic wires may be fashioned into a 'basket' configuration to form a magnetic wire basket, which can more easily capture a superparamagnetically-labeled stone fragment.

In one embodiment, a medical device and method is provided for retrieval and elimination of calculi (stone fragments) from the urinary tract. A plurality of magnets is arranged to form a flexible wire (MagWIRE). The magnets are magnetically attached to each other, end-to-end, and arranged with their magnetic polarities alternating in direction. In one example, the alternating end-to-end polarities alternate 180 degrees or they could alternate with a rotation from magnet to magnet at 45-180 degree increments (for example forming a Halbach array). In one embodiment, the magnets may be enclosed by a flexible sheath to ensure the structural stability of the wire. In another embodiment, the magnets may be ring-shaped with a wire running through the centers of the rings to ensure structural stability. The absence of an outer sheath in this latter embodiment can increase the maximum magnetic gradient encountered at the surface of the wire.

The magnetization direction of each of the magnets is orthogonal to the length axis of the flexible wire. There could be 10 to 1000 magnets forming the flexible wire with each of the magnets having a length in a range of 0.5 mm to 10 cm. In one example, the magnets are cylindrical magnets (rods) each having a diametric magnetization, however, the magnets do not have to be cylindrical, and could have other shapes including rings. In case of cylindrical and ring magnets they could have a diameter of 0.2 mm to 10 mm. In case of ring magnets, there can be a stainless steel wire in the center of the rings to further augment the effective magnetic field gradient.

In one variation to this embodiment, there could additionally be non-magnetic spacers in between each magnetic unit, as a means to even further increase the magnetic field gradient along the wire.

The wire may have magnets only in the tip of the wire, having a total length of 1 to 20 cm. The total length of the wire may range from 50 to 200 cm. The remainder of the wire may be comprised by a non-magnetic stylet, which serves to provide increased stiffness to that portion of the wire. This stylet could then be removed from the wire to render that portion flexible again. A stiffened wire will be easier to load into the working channel of a standard ureteroscope. The tip of the ureteroscope is flexible to allow for better navigation and visualization. A stiff wire within the working channel limits the flexibility of the tip. Thus, subsequently removing the inner stylet will allow the tip of the ureteroscope to regain its flexibility.

The medical device is dimensioned so that it can be introduced into the urinary tract. This is typically through the sheath or working channel of an endoscopic device such as a cystoscope, ureteroscope, or nephroscope. These sheaths may be as large as 30 Fr (1 cm in diameter). The device may also be introduced through the working channel of a ureteroscope, which is typically 3.6 Fr (1.2 mm). It may also be introduced through a ureteral access sheath, which is typically 11-12 Fr (3.5-3.8 mm in inner diameter). The medical device is further dimensioned to allow for removal from the sheath with stone fragments attached to it, which functionally increases the diameter of the wire depending on the size of the fragment.

The magnetic field along the length axis is sufficient to attract to the surface of the flexible wire superparamagnetic particles, which could bind themselves to calculi which could be composed of calcium, uric acid, struvite, or cystine. The flexible wire is a self-contained device (i.e. without the use of an external magnetic source) which could generate magnetic field gradients of 100 to 10,000 T/m. The stone fragments are then displaceable from the surface of the magnets or outer sheath with manual force, allowing for re-use of the magnetic wire. In one embodiment, the magnets themselves can be removed from an outer sheath, thus removing the magnetic force and allowing the fragments to be more easily displaced from the sheath.

The superparamagnetic particles can range in size from 5 nm to 5 microns. They may be functionalized with chemical groups that will bind to stone fragments composed of calcium, uric acid, struvite, or cystine, thus coating the surface of the fragment and rendering it magnetizable. In another embodiment, the particle solution is mixed with a hydrogel precursor polymer, which can also be functionalized with chemical groups that bind to the stone fragment. Upon cross-linking, the magnetic hydrogel will coat the stone fragments. This can provide a higher density of superparamagnetic particles to increase the magnetic force experienced by the fragments, as well as provide additional adhesives forces to facilitate stone fragment retrieval.

What is claimed is:

1. A method for removing calculi from a urinary tract, comprising:

inserting superparamagnetic particles into the urinary tract, wherein the superparamagnetic particles bind themselves to calculi, wherein the calculi are calcium, uric acid, struvite, cystine, or a combination thereof;

inserting a flexible magnet wire into the urinary tract, wherein the flexible magnet wire is positioned at an end of a flexible wire that is not magnetic, wherein the flexible magnet wire has a plurality of magnets arranged within a flexible sheath forming the flexible magnet wire, wherein the plurality of magnets are magnetically attached end-to-end and arranged with their magnetic polarities alternating in direction, and wherein a magnetic field along the length of the flexible magnet wire is sufficient to attract to the surface of the flexible magnet wire the superparamagnetic particles which have bound themselves to the calculi.

2. The method of claim 1, wherein the superparamagnetic particles are delivered with a hydrogel-forming polymer.

3. The method of claim 2, wherein the hydrogel-forming polymer is capable of cross-linking with the superparamagnetic particles bound to the calculi forming a magnetic hydrogel that coats and binds the calculi.

4. The method of claim 1, wherein the flexible magnet wire is resident within a working channel of a ureteroscope and inserting the flexible magnet wire into the urinary tract comprises inserting the ureteroscope into the urinary tract and extending the flexible magnet wire from the working channel.

5. The method of claim 1, wherein the superparamagnetic particles range in size from 5 nm to 5 microns.

6. The method of claim 1, further comprising:

removing the flexible magnet wire from the urinary tract; and removing the magnetized calculi from the flexible magnet wire.

7. The method of claim 6, further comprising:

reinserting the flexible magnet wire into the urinary tract following removal of the magnetized calculi from the flexible magnet wire.

8. The method of claim 1, wherein the flexible magnet wire is configured as a magnet wire basket.

9. The method of claim 1, wherein the sheath is configured to facilitate removal of the magnetized calculi from the flexible magnet wire.

10. The method of claim 1, wherein the sheath includes bristles extending therefrom, the bristles being configured to promote attraction of the superparamagnetic particles bound to the calculi to the flexible magnet wire.

11. The method of claim 1, wherein each of the plurality of magnets are diametrically magnetized.

12. The method of claim 1, wherein the magnetization direction of each of the plurality of magnets is axial to the length axis of the magnet.

13. The method of claim 1, wherein the magnetization direction of each of the plurality of magnets is at least one of orthogonal to the length axis of the magnet and axial to the length axis of the magnet.

14. A method comprising:

introducing superparamagnetic particles into the urinary tract, wherein the superparamagnetic particles bind themselves to calculi, wherein the calculi are calcium oxalate, uric acid, struvite, cystine, or a combination thereof;

inserting a ureteroscope with a flexible magnet wire resident within a working channel of the ureteroscope into the urinary tract, wherein the flexible magnet wire is positioned at an end of a flexible wire that is not magnetic;

extending the flexible magnet wire out of the working channel and into the urinary tract thereby magnetically attracting the superparamagnetic particles bound to the calculi to the flexible magnet wire;

removing the flexible magnet wire with the superparamagnetic particles bound to the calculi attracted thereto from the urinary tract prior, thereby removing the calculi from the urinary tract.

15. The method of claim 14, further comprising:

removing the magnetized calculi from the flexible magnet wire.

16. The method of claim 15, further comprising:

reinserting the flexible magnet wire into the urinary tract following the removing of the magnetized calculi from the flexible magnet wire.

17. The method of claim 14, wherein the flexible magnet wire has a plurality of magnets arranged within a flexible sheath forming the flexible magnet wire, wherein the plurality of magnets are magnetically attached end-to-end and arranged with their magnetic polarities alternating in direction.

18. The method of claim 17, wherein the magnetization direction of each of the plurality of magnets is orthogonal to the length axis of the flexible magnet wire.

19. The method of claim 14, wherein a magnetic field along the length of the flexible magnet wire is sufficient to attract to the surface of the flexible magnet wire the superparamagnetic particles that are in contact with the calculi.

20. The method of claim 14, wherein the flexible magnet wire is configured as a magnet wire basket.

21. The method of claim 14, wherein the flexible magnet wire is covered by a sheath.

22. The method of claim 21, wherein the sheath is configured to facilitate removal of the magnetized calculi from the flexible magnet wire.

23. The method of claim 21, wherein the sheath includes bristles extending therefrom, the bristles being configured to promote attraction of the superparamagnetic particles bound to the calculi to the flexible magnet wire.

\* \* \* \* \*